United States Patent

Komi

Patent Number: 5,728,045
Date of Patent: Mar. 17, 1998

[54] ENDOSCOPE HAVING AUXILIARY HOLE

[75] Inventor: Shuji Komi, Omiya, Japan

[73] Assignee: Fuji Photo Optical Co., Ltd., Saitama, Japan

[21] Appl. No.: 572,882

[22] Filed: Dec. 18, 1995

[30] Foreign Application Priority Data

Dec. 26, 1994 [JP] Japan ................................. 6-337237

[51] Int. Cl.[6] ............................................. A61B 1/12
[52] U.S. Cl. ................................. 600/156; 600/153
[58] Field of Search ....................... 600/101, 104, 600/139, 153, 156, 157; 604/27, 35, 902

[56] References Cited

U.S. PATENT DOCUMENTS

| | | | |
|---|---|---|---|
| 3,051,176 | 8/1962 | Alberti | 600/156 X |
| 4,959,058 | 9/1990 | Michelson | 600/156 X |
| 5,320,091 | 6/1994 | Grossi et al. | 600/156 X |

FOREIGN PATENT DOCUMENTS

| | | | |
|---|---|---|---|
| 1255820 | 10/1989 | Japan | 600/156 |
| 001309 | 2/1989 | WIPO | 600/156 |
| 9410896 | 5/1994 | WIPO | 600/156 |

*Primary Examiner*—Beverly M. Flanagan
*Attorney, Agent, or Firm*—Townsend&Banta

[57] ABSTRACT

An endoscope which is capable of appropriately sucking air in the stomach in endoscopic retrograde cholangiopancreatography, and which is capable of feeding and sucking a liquid and air at a portion other than the end portion. The endoscope comprises: an end portion which is also used as a suction hole and which is provided with a forceps insertion; a bendable flexible portion; and an auxiliary hole disposed in an outer peripheral groove formed in the middle of the flexible portion separately from the forceps insertion hole. An auxiliary receiving portion at the operating portion is connected to the auxiliary portion through a supply pipe. It is possible to feed or suck water or air from the flexible portion by mounting a syringe or the like in the auxiliary receiving hole. Since the auxiliary hole is disposed in the outer peripheral groove, sucking or feeding is not obstructed by a wall or the like in the body under observation.

2 Claims, 3 Drawing Sheets

5,728,045

ENDOSCOPE HAVING AUXILIARY HOLE

BACKGROUND OF THE INVENTION

This application claims the priority of Japanese Patent Application No. 6-337237 filed on Dec. 26, 1994.

1. Field of the Invention

The present invention relates to a structure of sucking and feeding a liquid or air in an endoscope the end portion of which is inserted into the body as the object of inspection.

2. Description of the Related Art

FIG. 5 shows the structure of the end portion of a side-looking type electronic endoscope as an example of a conventional endoscope. The end portion 1 is connected to a bendable flexible portion 2. An irradiation window 3 to which a light guide is connected and an observation window 4 to which a CCD (Charge Coupled Device) is attached are arranged on the side surface of the end portion 1. A forceps insertion hole 6 which communicates with a manipulating tool insertion channel 5 is disposed in the vicinity of these members, and a raising table 7 is disposed in the forceps insertion hole 6 so as to be rotatable around a shaft 8. A wire 9 is connected to the raising table 7, and by pulling the wire 9, it is possible to lead a manipulating tool which is inserted into the manipulating tool insertion channel 5 to a predetermined position in the body under observation.

The forceps insertion hole 6 also serves as a suction hole, and it is possible to discharge air and a liquid in the body under observation to the outside by sucking them through the manipulating tool insertion channel 5. A nozzle for washing 10 is disposed in the vicinity of the irradiation window 3 and the observation window 4, and it is possible to wash the irradiation window 3 and the observation window 4 by jetting water and air from the nozzle 10.

Such a conventional electronic endoscope has the following problem at the time of observation or treatment from the mammilation of the duodenum. As an example of the treatment from the mammilation of the duodenum, there is endoscopic retrograde cholangiopancreatography (ERCP) for observing the pancreatic duct and the bile duct by an X-ray apparatus. In this case, a contrast medium is poured from the mammilation into the pancreatic duct and the bile duct by using the endoscope. FIG. 4 explains this treatment. In FIG. 4, the end portion 1 of the endoscope is inserted into the duodenum 13 through the stomach 12, so as to lead the end portion 1 to the mammilation 16, which opens into the pancreatic duct 14 and the bile duct 15. In this state, the manipulating tool is led from the forceps insertion hole 6 at the end portion 1 to the mammilation 16, and a predetermined treatment such as pouring of a contrast medium is conducted with the manipulating tool.

However, when the stomach 12 is inflated as indicated by the broken line in FIG. 4, a part of the pancreatic duct 14 and the bile duct 15 containing the contrast medium is concealed behind the inflating stomach 12, thereby making it difficult to observe. The stomach 12 sometimes inflates naturally, and it is sometimes inflated for the purpose of observation. In such a case, if it is possible to suck air in the stomach 12 from the flexible portion 2, it is convenient. In addition, if it is possible to feed or suck a liquid or air at a portion other than the end portion, an endoscope may be used for another purpose and the application range of an endoscope will be enlarged.

SUMMARY OF THE INVENTION

Accordingly, it is an object of the present invention to eliminate the above-described problem in the related art and to provide an endoscope having an auxiliary hole which is capable of appropriately sucking air in the stomach in endoscopic retrograde cholangiopancreatography, and which is capable of feeding and sucking a liquid or air at a portion other than the end portion when the endoscope is used for another purpose.

To achieve this end, an endoscope according to the present invention comprises: an end portion which is also used as a suction hole and which is provided with a forceps insertion hole for leading a manipulating tool therethrough;

a flexible portion which is connected to the end portion; and an auxiliary hole disposed in the middle of the flexible portion separately from the forceps insertion hole at the end portion so as to feed and suck a liquid or air therethrough.

It is preferable to connect an auxiliary receiving hole to the auxiliary hole through a supply pipe. The auxiliary receiving hole is disposed in the operating portion of the endoscope.

It is also preferable to form a groove in the outer periphery of the flexible portion and to provide an auxiliary hole in the groove.

According to this structure, if a syringe or the like is disposed in the auxiliary receiving hole, it is possible to supply air and water from the auxiliary hole of the flexible portion into the body as the object of inspection, and also possible to suck air or the like from the body. It is therefore possible to suck air in the stomach from the flexible portion during endoscope retrograde cholangiopancreatography, and to obtain a picture which is easy to observe.

Since it is possible to form an outer peripheral groove in the flexible portion and to provide the auxiliary hole in the outer peripheral groove, it is easy to suck air and water even in the case in which the body under observation is in contact with the flexible portion.

The above and other objects, features and advantages of the present invention will become clear from the following description of the preferred embodiment thereof, taken in conjunction with the accompanying drawings.

DESCRIPTION OF THE PREFERRED EMBODIMENT

Figure 1:
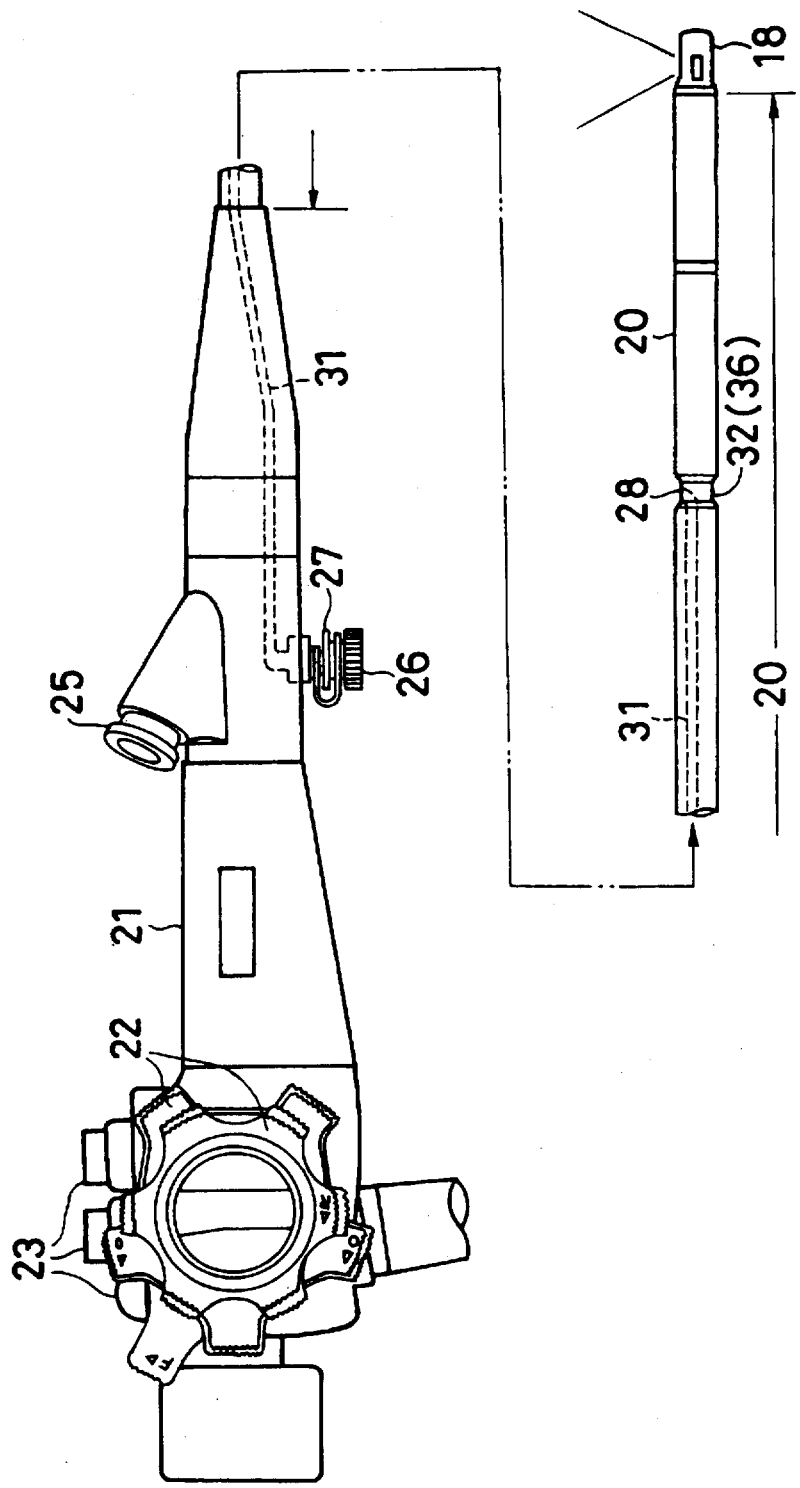
FIG. 1 shows the entire structure of an embodiment of an endoscope having an auxiliary hole according to the present invention.
Figure 2:
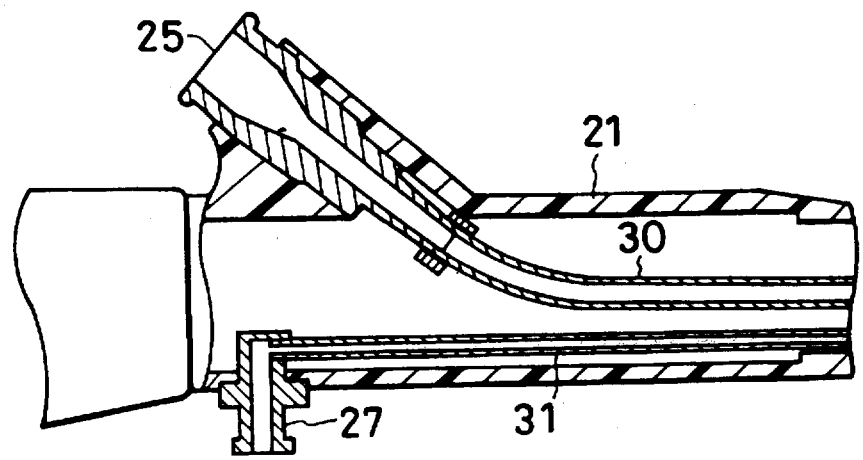
FIG. 2 is a sectional view of the interior of the front side of the operating portion of the embodiment.
Figure 3A:
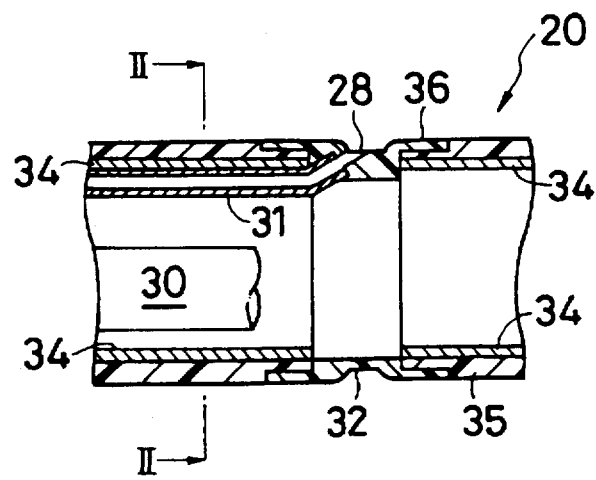
FIG. 3(A) is an enlarged sectional view of the interior of a flexible portion provided with the auxiliary hole.
Figure 3B:
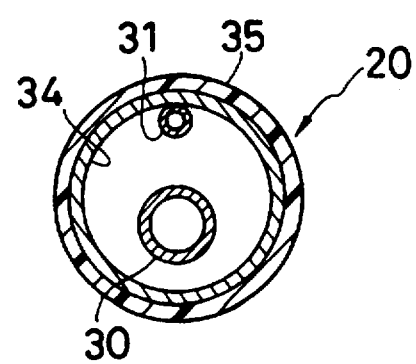
FIG. 3(B) is a sectional view of the flexible portion shown in FIG. 3(A), taken along the line II—II.
Figure 5:
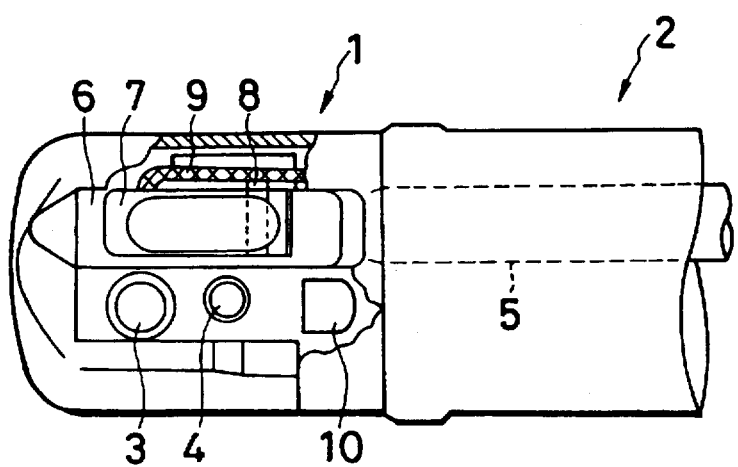
FIG. 5 is a side elevational view of the structure of the end portion of a conventional endoscope.

FIGS. 1,2,3A and 3B show the structure of an embodiment of an electronic endoscope according to the present invention, wherein FIG. 1 shows the entire structure, FIG. 2 is a sectional view of the structure of the front side of the operating portion, and FIGS. 3(A) and 3(B) are enlarged view of an auxiliary hole provided at a flexible portion. As shown in FIG. 1, the endoscope is composed of an end portion 18 similar to the end portion shown in FIG. 5, a flexible portion 20 and an operating portion 21 which is grasped by an operator or the like. The operating portion 21 is provided with a rotary knob 22 and an operation button 23 for bending the end portion 18, and a manipulating tool insertion hole 25 for inserting a manipulating tool therethrough and an auxiliary receiving hole 27 having a cap 26 are provided on the front side of the operating portion 21. An auxiliary hole 28 is provided in the middle of the flexible portion 20, preferably at a distance of 200 mm to 500 mm (the effective length of the endoscope is about 1000 mm) from the end portion (the forward end of the end portion 18).

On the front side of the operating portion 21, the manipulating tool insertion hole 25 communicates with a manipulating tool insertion channel 30, and the manipulating tool insertion channel 30, in turn, communicates with a forceps insertion hole formed in the side surface of the end portion 18, as shown in FIG. 2. The auxiliary receiving hole 27 is connected to a supply pipe 31, and the supply pipe 31 is connected to the auxiliary hole 28.

The auxiliary hole 28 is provided in an outer peripheral groove 32 formed in the flexible portion 20, as shown in FIG. 3(A). The flexible portion 20 is composed of a flexible pipe 34 produced by connecting a multiplicity of metal rings, and a coating 35 of a resin material which coats the flexible pipe 34. A ring member 36 of a resin (electric insulating material) is inserted in the middle of the flexible pipe 34 by, for example, enlarging the space between the metal rings or cutting a part of the connected metal rings, and the outer peripheral groove 32 is formed in the ring member 36. The auxiliary hole 28 is formed in the outer peripheral groove 32, as shown in FIG. 3(A), and the supply pipe 31 is connected to the auxiliary hole 28. It goes without saying that the auxiliary hole 28 may be formed in the wall of the metal ring without changing the structure of the flexible pipe 34.

Figure 4:
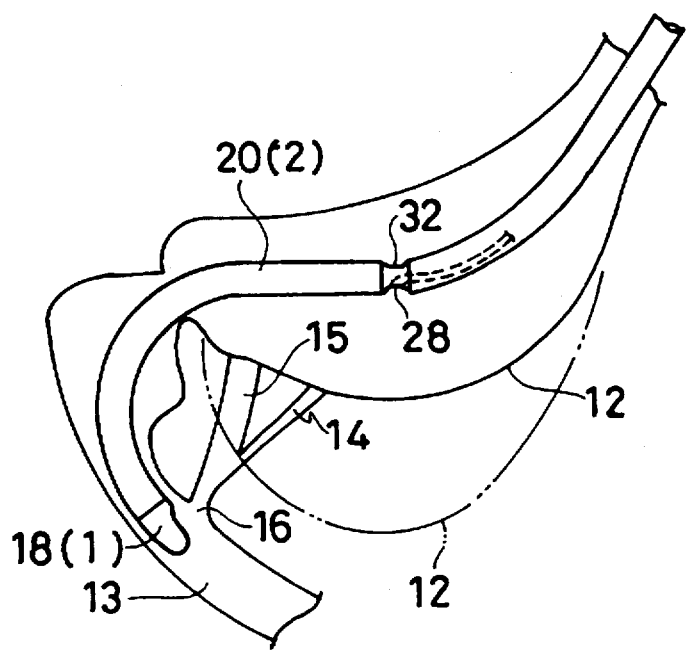
FIG. 4 shows the embodiment actually applied to digestive organs.

The operation of the embodiment of the endoscope of the present invention having the above-described structure will now be explained. In this example, the endoscope is applied to endoscopic retrograde cholangiopancreatography shown in FIG. 4. The endoscope is inserted into the duodenum 13 through the stomach 12, so as to lead the end portion 18 to a position at which observation of the mammilation 16 is possible. In this state, the manipulating tool is led from the manipulating tool insertion hole 25 to the forceps insertion hole through the manipulation insertion channel 30. If the stomach 12 is inflated as indicated by the broken line in FIG. 4, a syringe, for example, is mounted in the auxiliary receiving hole 27 and air in the stomach 12 is sucked through the auxiliary hole 28. Then the stomach 12 deflates as indicated by the solid line (or to a larger extent) in FIG. 4. A contrast medium is poured from the mammilation 16 into the pancreatic duct 14 and the bile duct 15 with the manipulating tool, and the conditions of the mammilation 16, the pancreatic duct 14, the bile duct 15, the cholecyst or the like are clearly observed by fluoroscopy In this embodiment, since the auxiliary hole 28 is provided in the outer peripheral groove 32 of the flexible portion 20, suction is not obstructed even if a wall of the stomach comes into contact with the flexible portion 20. In addition, provision of the auxiliary hole 28 in the outer peripheral groove 32 is advantageous in that it is possible to confirm the position of the auxiliary hole 28. To state this concretely, in fluoroscopy, the ring member 36 in which the outer peripheral groove 32 is confirmed as a break in the flexible pipe 34, so that the position of the auxiliary hole 28 is confirmed. If a metal member is disposed on the underside of the ring member 36, it is easy to confirm the groove portion by a difference in the level.

Although the embodiment is applied as an endoscope for the stomach and intestines or to endoscopic retrograde cholangiopancreatograph, the endoscope of the present invention is usable for other parts of the body and for various treatments, inspections and observations. In such a case, the auxiliary hole 28 is set at the optimal position in the flexible portion 20 of the endoscope.

As explained above, according to the present invention, an auxiliary hole is provided in the middle of the flexible portion separately from the forceps insertion hole, and a liquid and air are fed and sucked through the auxiliary hole, it is possible to feed and suck a liquid and air at a portion other than the end portion, so that the application range of the endoscope is enlarged. In endoscopic retrograde cholangiopancreatography, it is possible to suck air in the stomach through the auxiliary hole, thereby facilitating the observation of the pancreatic duct, the bile duct, etc.

In addition, since the auxiliary hole is provided in the groove formed in the outer periphery of the flexible portion, even a wall in the body as the object of inspection is in contact with the flexible portion, it is easy to suck and feed air or a liquid, and it is also easy to confirm the position of the auxiliary hole.

While there has been described what is at present considered to be a preferred embodiment of the invention, it will be understood that various modifications may be made thereto, and it is intended that the appended claims cover all such modifications as fall within the true spirit and scope of the invention.

What is claimed is:

1. An endoscope having an auxiliary hole comprising:

a flexible portion connected at one end to an end portion and at another end to an operating portion;

said operating portion having a forceps insertion hole for leading a manipulating tool therethrough said forceps insertion hole also serving as a suction hole;

said flexible portion having an outer peripheral groove disposed in the middle thereof;

an auxiliary hole disposed in said outer peripheral groove separately from said forceps insertion hole at said operating portion, said auxiliary hole adapted to feed and suction a liquid or air therethrough.

2. An endoscope having an auxiliary hole according to claim 1, further comprising:

a supply pipe connected at one end to said auxiliary hole; and an auxiliary receiving hole disposed in the operating portion of said endoscope, said auxiliary receiving hole being connected to another end of said supply pipe.

* * * * *